US009241866B2

(12) United States Patent
Golan

(10) Patent No.: US 9,241,866 B2
(45) Date of Patent: Jan. 26, 2016

(54) SEXUAL AID DEVICE WITH AUTOMATIC OPERATION

(71) Applicant: Shoham Golan, Netanya (IL)

(72) Inventor: Shoham Golan, Netanya (IL)

( * ) Notice: Subject to any disclaimer, the term of this patent is extended or adjusted under 35 U.S.C. 154(b) by 140 days.

(21) Appl. No.: 13/995,091

(22) PCT Filed: Dec. 30, 2012

(86) PCT No.: PCT/IL2012/050561

§ 371 (c)(1),
(2) Date: Jun. 17, 2013

(87) PCT Pub. No.: WO2013/098824

PCT Pub. Date: Jul. 4, 2013

(65) Prior Publication Data

US 2014/0066699 A1 Mar. 6, 2014

Related U.S. Application Data

(63) Continuation of application No. 13/341,966, filed on Dec. 31, 2011, now abandoned, and a continuation of application No. 13/563,186, filed on Jul. 31, 2012, now abandoned.

(51) Int. Cl.
*A61F 5/00* (2006.01)
*A61H 19/00* (2006.01)

(52) U.S. Cl.
CPC ................ *A61H 19/44* (2013.01); *A61H 19/50* (2013.01); *A61H 2201/0103* (2013.01);
(Continued)

(58) Field of Classification Search
CPC .... A61H 23/0218; A61H 19/40; A61H 19/44
USPC ....................... 600/38–41; 601/118, 151, 153
See application file for complete search history.

(56) References Cited

U.S. PATENT DOCUMENTS 4,594,997 A 6/1986 Hakky
5,063,914 A 11/1991 Cowen
(Continued)

FOREIGN PATENT DOCUMENTS

NL 1003501 A1 8/1996
WO WO-2008090306 A1 7/2008

OTHER PUBLICATIONS https://web.archive.org/web/20110227110951/http://psigasm.net/? "Anal contractions of a man during orgasmic masturbation.".
(Continued)

*Primary Examiner* — Samuel Gilbert
(74) *Attorney, Agent, or Firm* — Venable LLP; Robert Kinberg; Jeffri A. Kaminski

(57) ABSTRACT

A sexual aid device, for allowing a user being a first party of sexual relationship with a second party, to simulate the physiologic reaction of the penis of a human male. The proposed sexual aid device includes a hollow penis body made of flexible or semi-rigid material and containing a plurality of telescopic sections for causing the penis body to be in its erected state when the telescopic sections are maximally propagated and for allowing the penis body to be in its descended default state, when the telescopic sections are maximally contracted; a simulated scrotum made of flexible or semi-rigid material, having a compartment for containing a mechanism for powering the propagation and contraction of the telescopic sections; a mechanism for providing a driving force required for powering the propagation and contraction of the telescopic sections; sensors located on the penis body, for detecting physical contact of the penis body with the body of the second party; a controller for controlling the driving force to cause the telescopic sections to maximally propagate, according to input signals received from the sensors and to time and to return to be maximally contracted, after a predetermined time; a power source for powering the controller and for generating the driving force; and a coupling mechanism for attaching the sexual aid device to the body of the first party.

11 Claims, 4 Drawing Sheets

(52) U.S. Cl.
CPC .. *A61H 2201/1215* (2013.01); *A61H 2201/149* (2013.01); *A61H 2201/1463* (2013.01); *A61H 2201/5028* (2013.01); *A61H 2201/5058* (2013.01); *A61H 2201/5082* (2013.01)

(56) References Cited

U.S. PATENT DOCUMENTS

| | | | | |
|---|---|---|---|---|
| 5,904,671 | A | 5/1999 | Navot et al. | |
| 6,350,230 | B1 | 2/2002 | Kontos | |
| 6,632,185 | B2 * | 10/2003 | Chen | 601/101 |
| 6,695,770 | B1 * | 2/2004 | Choy et al. | 600/38 |
| 8,360,956 | B2 * | 1/2013 | Squicciarini | 600/38 |
| 2005/0234292 | A1 | 10/2005 | Faulkner et al. | |
| 2008/0194907 | A1 | 8/2008 | Lin et al. | |
| 2009/0038069 | A1 | 2/2009 | Heilman | |
| 2009/0177029 | A1 | 7/2009 | Alilovich | |
| 2011/0009693 | A1 | 1/2011 | Borrero | |
| 2011/0034837 | A1 | 2/2011 | Lee | |
| 2011/0218395 | A1 | 9/2011 | Stout | |
| 2012/0022323 | A1 | 1/2012 | Forsell | |

OTHER PUBLICATIONS

Supplementary European Search Report of EP 12 85 2447 dated Jul. 28, 2015.

* cited by examiner

SEXUAL AID DEVICE WITH AUTOMATIC OPERATION

FIELD OF THE INVENTION

The invention disclosed herein relates generally to sexual aids. More particularly, the invention relates to a sexual aid device, which automatically emulates the human penis physiological behaviors.

BACKGROUND OF THE INVENTION

There is a growing acceptance of sexuality, as exhibited by popular acceptance of the near-universality of masturbation, and the growth of demands for sexual devices. Prior to these changes, many sexual aid devices were sold for sexual pleasure, although primarily under the euphemistic names and a pretense of providing massage services.

Modern sexual aid devices fall broadly into two classes: mechanized and non-mechanized. Mechanized devices typically vibrate, although there are types that can rotate, thrust, and even circulate small beads within an elastomeric shell. Non-mechanized devices, such as a dildo (an artificial erect penis, used as a sexual aid) to an erotic vibrator (a device often used to attain an orgasm by its vibration mechanism) are made from solid, rigid or semi-rigid materials in a variety of states and sizes.

Also, oral sex being an act of using the mouth, lips, and tongue to stimulate the female genitals became acceptable in many cultures. Oral sex is often accompanied by the insertion of fingers or a sexual aid into the vagina and/or into the anus, which allows simultaneous stimulation of the receptors in sexual pleasure zones, which many women consider capable of producing very intense experiences.

However, the available sexual aid devices, such as dildos and vibrators fail to emulate the human penis physiological behaviors, since they require manual activation and deactivation.

It is therefore an object of the present invention to provide a sexual aid device, which emulate the human penis physiological behavior, which is automatically activated and deactivated when used on a human male body upon being in contact with the female sexual areas.

Other purposes and advantages of the invention will appear as the description proceeds.

SUMMARY OF THE INVENTION

The present invention is directed to a sexual aid device, for allowing a user being a first party of sexual relationship with a second party, to simulate the physiologic reaction of the penis of a human male. The proposed sexual aid device comprises:

a) a hollow penis body made of flexible or semi-rigid material and containing a plurality of telescopic sections for causing the penis body to be in its erected state when the telescopic sections are maximally propagated and for allowing the penis body to be in its descended default state, when the telescopic sections are maximally contracted;

b) a simulated scrotum made of flexible or semi-rigid material, having a compartment for containing means for powering the propagation and contraction of the telescopic sections;

c) means for providing a driving force required for powering the propagation and contraction of the telescopic sections;

d) one or more sensors located on the penis body, for detecting physical contact of the penis body with the body of the second party;

e) a controller for controlling the driving force to cause the telescopic sections to maximally propagate, according to input signals received from the sensors and to time and to return to be maximally contracted, after a predetermined time;

f) a power source for powering the controller and for generating the driving force; and g) means for attaching the sexual aid device to the body of the first party.

The mechanism may be electro-mechanical and comprise:

- an electric motor having a rotatable axis;
- a rotatable threaded shaft connected to the axis via a mechanical transmission and to at least one telescopic section, being a leading section, via a mating threaded member;
- means for preventing the member from rotating, to thereby allow the member to be displaced along the rotatable threaded shaft during rotation; and
- a battery for powering the electric motor via the controller.

The leading section may comprise a rounded tip in its proximal edge, to reduce friction with the walls of the penis body. It also may comprise one or more projections that extend outwardly and penetrate corresponding guiding grooves formed along the internal wall of the penis body, to avoid rotation of the leading section when the threaded shaft rotates.

The sensors may be selected from the group of:

- an electric contact sensor, for closing an electric circuit;
- a humidity sensor;
- a temperature sensor.

The mechanism may also be pneumatic or hydraulic and may be adapted to change states in the sexual aid device inflating/deflating air into/from the penis body, to thereby stretch and shrink the outer covering parts of the penis body.

The controller may include:

- a processor for analyzing the data received from the sensors and for activating an erected state according to the results of the analysis; and
- a timer for deactivating the erected state after a predetermined time has been lapsed from activation.

The flexible or semi-rigid material may be selected from the group of:

- silicon;
- Rubber;
- Plastic;
- Latex.

The connection between the telescopic sections may be adapted to allow each section to change its angle with respect to its neighboring sections, to thereby allow movement along a curved path.

The rotation direction of the threaded shaft may be adapted to determine the sliding direction of the leading section, to thereby cause sections to propagate or to contract.

The means for attaching the sexual aid device to the body of the first party may include a belt or a sling with an appropriate buckle.

The first party may be a sex doll, which wears the sexual aid device. Alternatively, the sexual aid device may be implemented as an integral part of the body of the sex doll.

BRIEF DESCRIPTION OF THE DRAWINGS

The invention will now be described in connection with certain preferred embodiments with reference to the following illustrative figures so that it may be more fully understood.

In the drawings.

DETAILED DESCRIPTION OF PREFERRED EMBODIMENTS

The present invention discloses a sexual aid device for sexual stimulation purposes, which is automatically operated when being in contact with an organ or area of the user's body. The sexual aid device has a mechanism that enables simulating the male's penis erection and downfall of the human male physiologic reaction of the male penis is coming in contact with the female sexual organ or body parts.

The sexual aid device proposed by the present invention is adapted to change its state automatically, from a descended state, to an erected state, and vice versa, so as to simulate the human penis physiological behaviors automatically. The proposed sexual aid device includes an electro-mechanical mechanism that simulates the human male physiologic reaction of the male penis when the penis is coming in contact with the female sexual organ or other body parts.

According to one embodiment, the mechanism includes an open electric circuit, which is adapted to push the front part of the sexual aid device to its rear part, whenever its front part becomes in contact with the female body parts, such that both parts are closing an electric circuit. Once the electric circuit is closed, it activates the mechanism of the sexual aid device designated automatically to change the sexual aid device state from a descended state, to an erected state and optionally to enlarge its size.

The sexual aid device also includes a second electric circuit with a timer, which maintains the erected state for a predetermine time, even if the first electric circuit that activates the mechanism is open because of lack of contact with the female body for example, which opens the first electric circuit between the front and rear parts of the sexual aid device.

After the predetermine time of operation, the timer opens the second electric circuit, and the sexual aid device switches back to its descended (default) state.

The mechanism optionally includes computerized or electronic parts, an electric power source and a telescopic section that allows its enlargement by initiation the erection state after a predetermined delay, switching back to the descended state.

Figure 1:
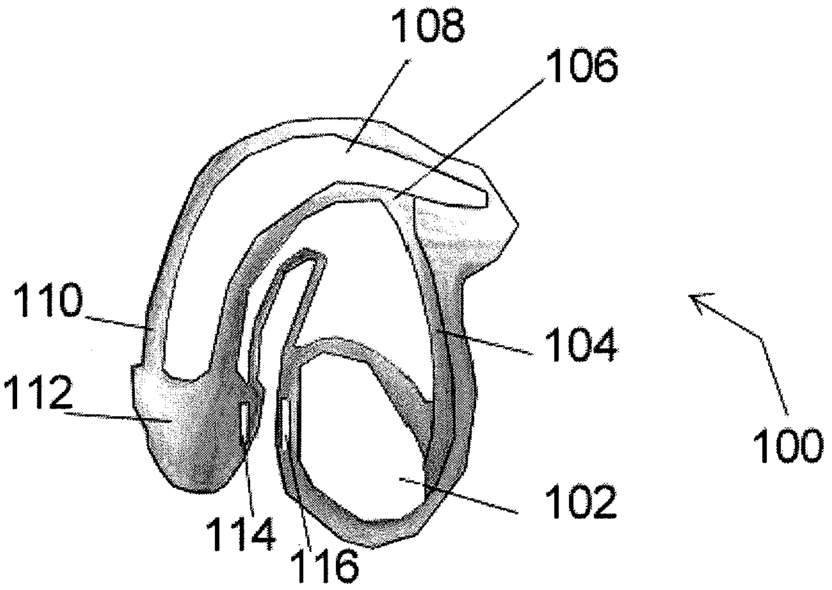
FIG. 1 is a schematic perspective view of the sexual aid device, in its default descended state, as in the present invention.

FIG. 1 is a schematic perspective view of the sexual aid device 100, in its descended (default) state. The mechanism simulates the male's penis erection and its physiologic reaction, whenever the sexual aid device becomes in contact with the female sexual organ or body parts.

Figure 2:
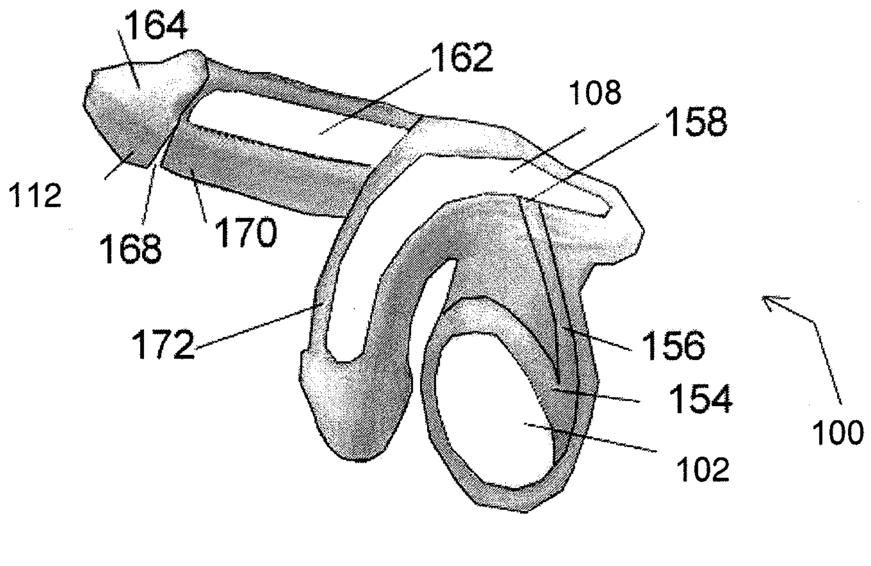
FIG. 2 is another schematic implementation of perspective view of the sexual aid device, showing the two states enabled by the sexual aid device of present invention.

One implementation of the sexual aid device 100 of the present invention includes a mechanism with an open electric circuit, where whenever the glans (front part) 112 of the sexual aid device 100 becomes in contact with the female body, it is pushed against the rear part 116 of the sexual aid device, and both parts 112 and 116 close an electric loop that activates the first electric circuit of the sexual aid device 100, which in turn activates the mechanism of the sexual aid device 100 to switch from a descended state, to an erected state and optionally to enlarge the size of the sexual aid device 100, as shown in FIG. 2.

Automatic switching between states requires a second electric circuit with a timer, which maintains the erected state for a predetermine time, even if the first electric circuit that operate the system and the mechanism is open because of lack of contact with the female body for example. In this case, the second electric circuit will maintain the sexual aid device 100 in the erected state. After the predetermine time of operation, the timer opens the second electric circuit, and the sexual aid device 100 switched back to its default state.

Section 102 (which emulates a scrotum) of the sexual aid device 100 optionally includes an electric power source (e.g., a battery which may be rechargeable) and a mechanism to implement the changes between states of the sexual aid device 100. For example, the mechanism enables changes in the sexual aid device 100 states by including an air inflating/deflating mechanism in the back section 102 that may be used to stretch and shrink the outer covering parts and materials of the sexual aid device, such as silicon or rubber cover.

The hollow section 108 in the sexual aid device 100 may be inflated by air through pipe 104 and 106, to stretch the outer cover parts and materials 110 of the sexual aid device 100, so as to shrink and to collapse them.

FIG. 2 is a perspective view of the sexual aid device 100, of the present invention, showing the two possible states: the enragement and erection state 164, and the descended state 172. The components of the mechanism and power source are located in section 102 of the sexual aid device 150, and has some extension passes through pipes 104, 154 and 158, to the hollow section 108 of the sexual aid device 100. When the mechanism is automatically operated, it streams air into hollow section 160 which inflates and when section 162 is filled with sufficient level of air pressure, it changes the default descended state 172, of the sexual aid device 100 switches to the erected state 164, to simulate the male penis erection. Such changes between states are enabled because the flexibility of the materials, the outer cover parts 170 and 172 are made of.

According to another embodiment, the sexual aid device 100 may be automatically controlled to switch to its erected state by pushing section 112 toward section 170 to close the gap 168 and to form electric contact that causes the first electric circuit to be closed and to activate the erection mechanism. Another optional implementation may act in a reverse action, such if the gap 168 is opened for predetermine time period, the system of the sexual aid device 150 will be closed and the sexual aid device will be returned to its default state 172.

Figure 3A:
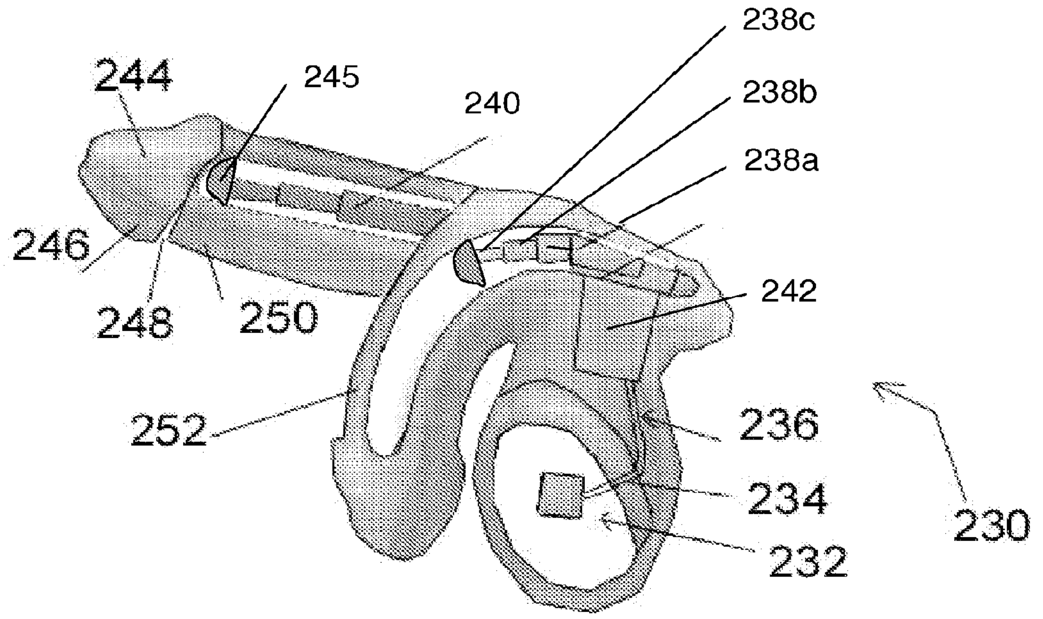
FIG. 3*a* is a schematic view of the internal mechanism of the sexual aid device of the present invention.

FIG. 3*a* is a schematic cross-sectional view of the mechanism that activates the sexual aid device 230, proposed by the present invention. The mechanism is located in cavity section 232 and comprises computerized or electronic circuitry (such as a controller) to activate and deactivate the erected state, an electric power source and mechanism to switch between states, according to predetermined rules and conditions. The mechanism includes several telescopic (tubular) sections 238*a*-238*c* with electric connections 236 and 234 to power source 232 that activates a propagation and contraction mechanism, such as an electric motor 242 that rotates a threaded shaft via a mechanical transmission. The shaft is engaged to the distal section 238*c* by a mating thread segment formed within the last section 238*c*. The last section 238*c* has a rounded tip 245 in its proximal edge, in order to make propagation and contraction smoother and easier, and to avoid substantial friction with (or even damage to) the flexible covering parts. The last section 238*c* has one or more projections that extend outwardly from the rounded tip 245 and penetrate corresponding guiding grooves formed along the internal wall of the hollow section 108, in order to avoid rotation of the last section 238*c*, when the threaded shaft rotates. This way, when the threaded shaft is rotated by the electric motor 242, the last section 238*c* slides along the formed guiding grooves, while rounded tip 245 changes the orientation of section 162. Also, the connection between the telescopic (tubular) sections allows each section to change its angle with respect to its neighboring sections, so as to allow movement along a curved path that section 162 forces while switching between states. The rotation direction of the threaded shaft (which is appropriately switched by the controller) determines the sliding direction of the last section 238*c* along the guiding grooves, thereby causing sections 238*a*-238*c* to propagate or to contract.

The enlargement and erection state 244 is reached when the telescopic sections 238*a*-238*c* are maximally propagated, and the descended state 252 is reached when the telescopic sections 238*a*-238*c* are maximally contracted.

According to another embodiment, by closing the gap 248 that causes the first electric circuit to be opened, the outer contact pushes section 246 toward section 250, thereby closing the gap 248 and closing the first electric circuit, which operates the second electric circuit that activate the mechanism of sexual aid device 230 to be in its erected state.

Figure 3B:
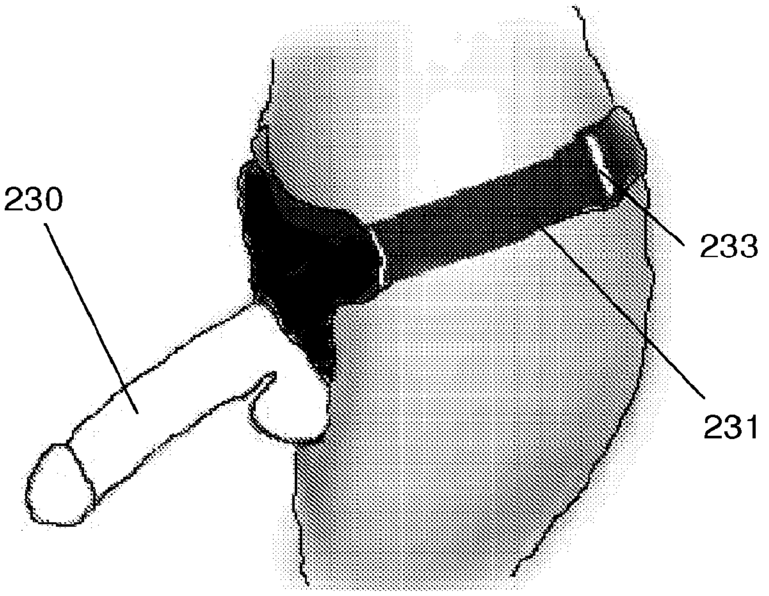
FIG. 3*b* shows an embodiment where the sexual aid device comprises means for attaching it to the body of the active party.

FIG. 3*b* shows an embodiment where the sexual aid device 230 also comprises means for attaching it to the body of the active party (usually the male), such as a belt 231 or a sling with an appropriate buckle 233.

Figure 3C:
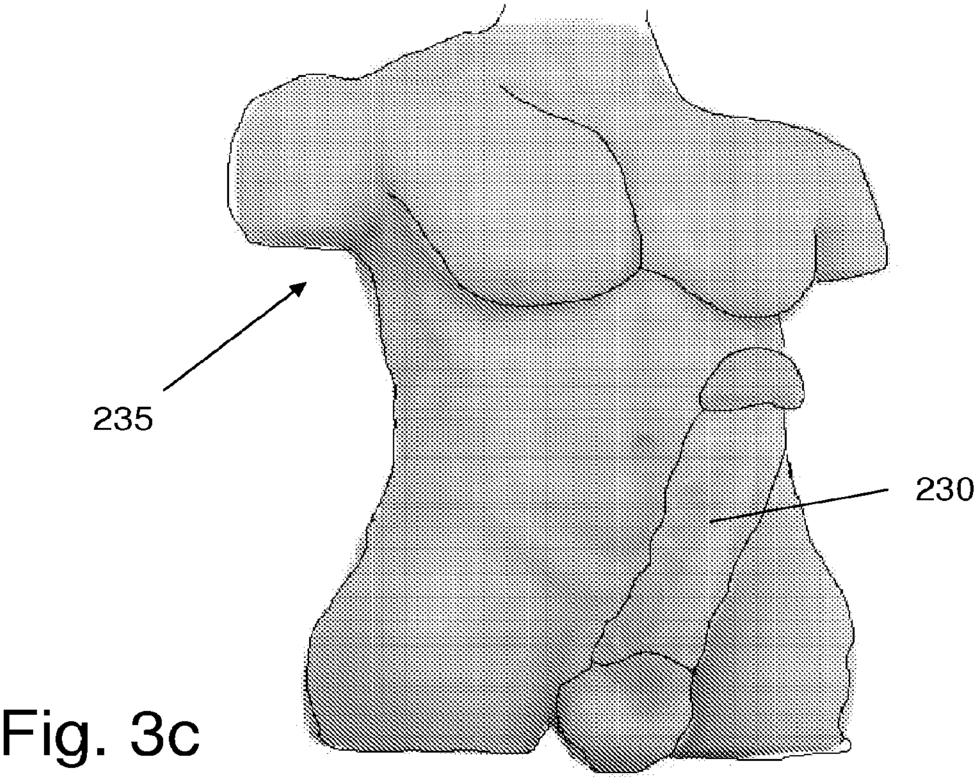
FIG. 3*c* shows an embodiment where the first party is a sex doll.

FIG. 3*c* shows an embodiment where the first party is a sex doll 235, which wears the sexual aid device 230 or alternatively, the sexual aid device 230 is implemented as an integral part of the body of the sex doll 235.

Figure 4:
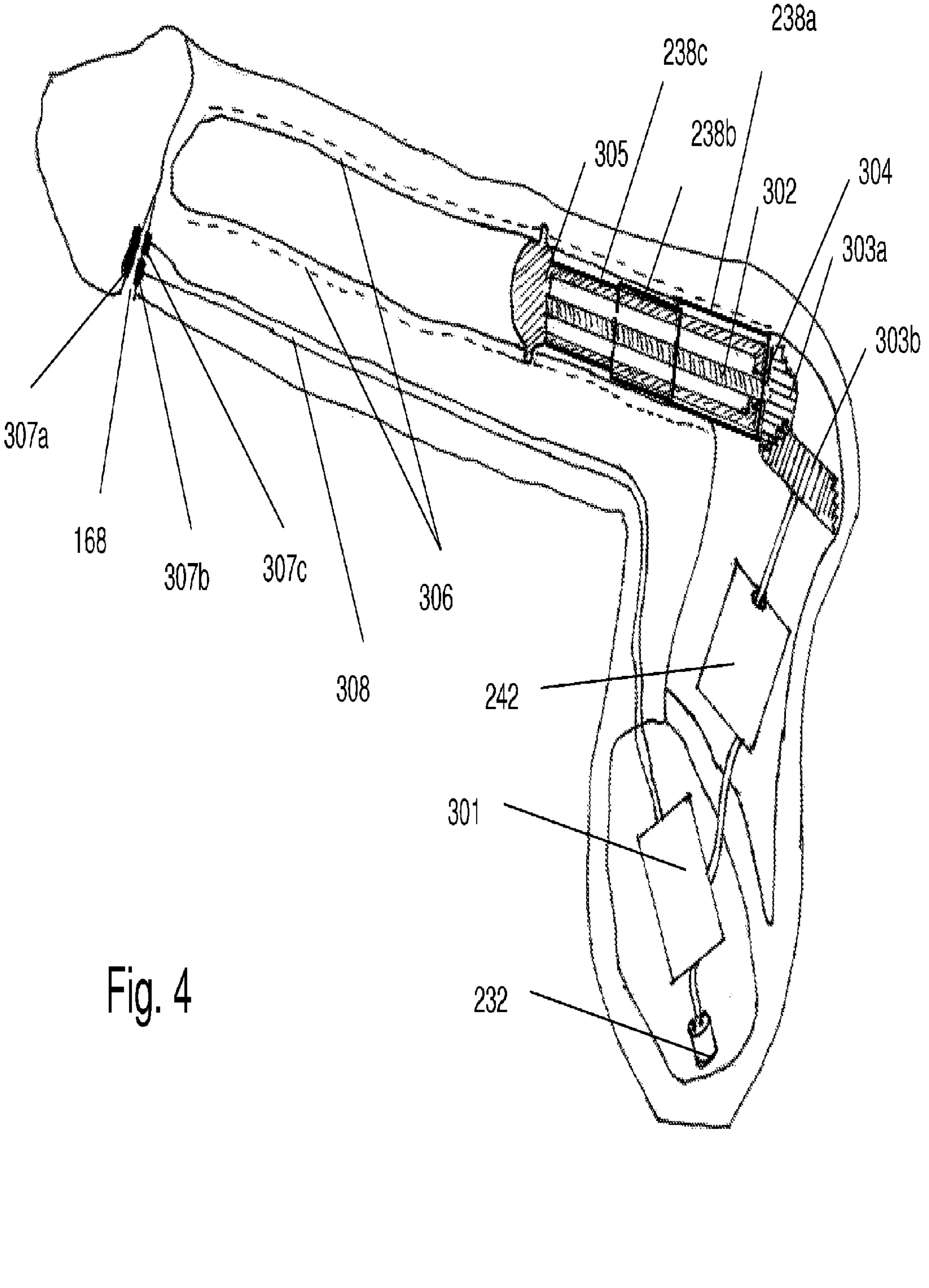
FIG. 4 is a cross-sectional view of the sexual aid device of the present invention.

FIG. 4 is a detailed cross-sectional view of the sexual aid device (shown in FIG. 3) of the present invention. The computerized or electronic circuitry (such as a controller) 301 activates deactivates the erected state.

The electric power source 232 provides power to the controller 301 and to the electric motor 242. The telescopic sections 238*a*-238*c* are driven to move by the last section 238*c*. Electric motor 242 rotates the threaded shaft 302 via a transmission of two perpendicular cogwheels 303*a* and 303*b* (with conical shape to obtain 90° rotational transmission). The mating thread segment 304 formed within the last section 238*c* is used to engage it to shaft 302. Rounded tip 245 of the last section 238*c* has two opposing projections 305 that penetrate corresponding guiding grooves 306 formed along the internal wall when the threaded shaft 302 rotates.

Sensors 307*a* to 307*c* may be attached to the glans 112, in order to detect an impending sexual activity, such as an intercourse or an oral sex act. In this case, the sensors may be humidity and/or temperature sensors that transmit an activation signal to the controller 301 (over wires 308), whenever the humidity of the body organs penetrates gap 168 and form a conduction path. Alternatively, the activation signal to the controller may be transmitted by temperature sensors that detect physical contact with the body of the passive party (normally the woman). Alternatively, the activation signal may be generated if sensors 307*a* to 307*c* are metallic contacts. In this case, whenever gap 168 is closed as a result of a physical contact, sensor 307*a* touches sensors 307*b* and 307*c* and thereby forms a conduction path (short-circuit) between them. This short-circuit is detected by the controller 301.

While some embodiments of the invention have been described by way of illustration, it will be apparent that the invention can be carried out with many modifications, variations and adaptations, and with the use of numerous equivalents or alternative solutions that are within the scope of persons skilled in the art, without exceeding the scope of the claims.

The invention claimed is:

1. A sexual aid device, for allowing a user being a first party of sexual relationship with a second party, to simulate the physiologic reaction of the penis of a human male, comprising:

a) a hollow penis body made of flexible or semi-rigid material and containing a plurality of telescopic sections for causing said penis body to be in its erected state when said telescopic sections are maximally propagated and for allowing said penis body to be in its descended default state, when said telescopic sections are maximally contracted;

b) a simulated scrotum made of flexible or semi-rigid material, having a compartment for containing means for powering the propagation and contraction of said telescopic sections;

c) means for providing a driving force required for powering the propagation and contraction of said telescopic sections;

d) one or more sensors located on said penis body, for detecting physical contact of said penis body with the body of said second party;

e) a controller for controlling said driving force to cause said telescopic sections to maximally propagate, according to input signals received from said sensors and to time and to return to be maximally contracted, after a predetermined time;

f) a power source for powering said controller and for generating said driving force; and g) means for attaching said sexual aid device to the body of said first party.

2. A sexual aid device according to claim 1, in which the means for providing a driving force is electro-mechanical and comprises:

an electric motor having a rotatable axis;

a rotatable threaded shaft connected to said axis via a mechanical transmission and to a leading one of the plurality of telescopic sections via a mating threaded member;

means for preventing said member from rotating, to thereby allow said member to be displaced along said rotatable threaded shaft during rotation; and a battery for powering said electric motor via the controller.

3. A sexual aid device according to claim 2, in which a rotation direction of the threaded shaft determines a sliding direction of the leading section, to thereby cause sections to propagate or to contract.

4. A sexual aid device according to claim 1, in which the leading section comprises a rounded tip in its proximal edge, to reduce friction with an internal wall of the penis body.

5. A sexual aid device according to claim 4, in which the leading section further comprises one or more projections that extend outwardly and penetrate corresponding guiding grooves formed along the internal wall of the penis body, to avoid rotation of said leading section when the threaded shaft rotates.

6. A sexual aid device according to claim 1, in which at least one of the sensors is selected from the group of:

an electric contact sensor, for closing an electric circuit;
a humidity sensor;
a temperature sensor.

7. A sexual aid device according to claim 1, in which the controller includes:

a processor for analyzing data received from the sensors and for activating an erected state according to results of the analysis; and a timer for deactivating said erected state after a predetermined time has been lapsed from activation.

8. A sexual aid device according to claim 1, in which the flexible or semi-rigid material is selected from the group of:

silicon;
Rubber;
Plastic;
Latex.

9. A sexual aid device according to claim 1, in which the means for attaching said sexual aid device to the body of the first party are a belt or a sling with an appropriate buckle.

10. A sexual aid device according to claim 1, in which the first party is a sex doll.

11. A sexual aid device according to claim 10, implemented as an integral part of the body of the sex doll.

* * * * *